United States Patent [19]

Harirchian et al.

[11] Patent Number: 5,300,657
[45] Date of Patent: Apr. 5, 1994

[54] PROCESS FOR PREPARING CHELIDONIC ACID

[75] Inventors: Bijan Harirchian, South Orange; John L. Gormley, Fair Lawn, both of N.J.

[73] Assignee: Lever Brothers Company, Division of Conopco, Inc., New York, N.Y.

[21] Appl. No.: 46,514

[22] Filed: Apr. 12, 1993

Related U.S. Application Data

[63] Continuation of Ser. No. 986,224, Dec. 7, 1992, abandoned.

[51] Int. Cl.$^5$ .......................................... C07D 309/38
[52] U.S. Cl. .................................................. 549/420
[58] Field of Search ........................................ 549/420

[56] References Cited

U.S. PATENT DOCUMENTS 3,759,833  9/1973  Easton et al. .
4,537,971  8/1985  Rebhahn et al. .

OTHER PUBLICATIONS

Riegel, Zwilgmeyer, Organic Syntheses Coll., vol. II, (1943) pp. 126–128.
Huang et al. CA 98(3):16549v (1983).

Primary Examiner—Nicky Chan
Attorney, Agent, or Firm—James J. Farrell

[57] ABSTRACT

Improved process for preparing chelidonic acid is disclosed.

8 Claims, No Drawings

PROCESS FOR PREPARING CHELIDONIC ACID

This is a continuation application of Ser. No. 07/986,224 filed Dec. 7, 1992, now abandoned.

BACKGROUND OF THE INVENTION

This invention relates to improved processes for preparing chelidonic acid, a precursor to chelidamic acid and a metal sequestering agent.

A known synthetic route to chelidonic acid uses a multi-step reaction of diethyloxalate, sodium ethoxide and acetone in ethanol.

Riegel, Zwilgmeyer, Organic Syntheses Coll., Vol. II, 126 (1943) and Huang et al. CA 98(3):16549v describe the preparation of chelidonic acid. In a first step rapid addition of 1.03 equivalents of diethyloxalate and 1 equivalent of acetone to a slight excess of sodium ethoxide yields ethyl dioxovalerate as the major product. In a second step another equivalent of diethyloxalate and hot sodium ethoxide solution is quickly added to the reaction causing a Claisen condensation with ethyl dioxovalerate. Acetone diethyloxalate ester is formed and exists as a disodium complex. In a third step ethanol is distilled off resulting in a cake-like product. In a further step, disodium acetone diethyloxalate complex is converted to its hydrogenated form by rapid, cold neutralization with hydrochloric acid. In a fifth step the neutralized acetone diethyloxalate is returned to the reactor after filtering and another equivalent of HCl added to promote cyclization and refluxed. The resulting chelidonic acid is cold filtered.

SUMMARY OF THE INVENTION

The present invention provides a process for the manufacture of chelidonic acid comprising the steps of:

(i) mixing metal alkoxide, dialkyl oxalate and an alcohol together in a reaction vessel;

(ii) stirring the mixture of (i) while adding acetone at a rate such that the concentration of acetone in the reaction mixture is not greater than 30% of the dialkyl oxalate and metal alkoxide together;

(iii) neutralizing the product of (ii) with acid;

(iv) refluxing to form chelidonic acid.

We have found that all required metal alkoxide, dialkyl oxalate and alcohol can be mixed together without any unfavorable reactions. This allows the addition of acetone to the stirred mixture at a rate such that the concentration of acetone in the reaction mixture is not greater than 30% of the dialkyl oxalate and metal alkoxide together, that is between 0% and 30%, preferably between 5% and 30%, without the need to rapidly add reagents in two steps as in the prior art. This manner of addition lessens the possibility of Aldol and self-Claisen condensations which can lower the yield.

The resulting acetone dialkyloxalate dimetal complex precipitates out of solution and thus is not affected by the presence of alcohol. This obviates the need to distill off excess alcohol which is an undesirable feature of the prior art and indeed gives the advantage that it allows mixing to continue essentially up to quantitative formation of the acetone dialkyloxalate. Even after cooling it is still possible to stir the mixture so that neutralization can be achieved without removing the product from the reaction vessel.

DETAILED DESCRIPTION OF THE INVENTION

The process taught in the prior art for the preparation of chelidonic acid has inherent deficiencies which result in lowering of the yield. As mentioned above, Aldol and/or self-Claisen condensation can produce an unwanted bis-$\beta$-diketone. In a separate step excess ethanol is distilled off in an attempt to drive the reaction to completion. We have found that this practice can cause lowering of the yield due to decomposition of the product.

An additional advantage of the process according to the invention is that acetone dialkyloxalate can be converted directly to chelidonic acid by reflux of the acid neutralized product without filtering or other cleaning steps which are necessary using the prior art process.

We have found that the process according to the invention enables chelidonic acid to be prepared in yields up to 95% compared to up to 79% as taught in the art.

In the process according to the invention, acetone is preferably added to the mixture of reagents at a rate that ensures that all of the acetone reacts without the concentration of acetone rising above 30%. In this manner the possibility of unwanted reactions is minimized.

It is preferred that the temperature of the mixture be raised towards the end of the acetone addition and that excess alcohol be used since it facilitates easy mixing of the reactants.

Preferably during the course of the process, the reagents are mixed in a molar ratio of metal alkoxide:dialkyloxalte:acetone of from 2:2:1 to 2.5:2.5:1. More preferably 2.1:2.1:1.

Metal alkoxides suitable for use in the present invention are sodium methoxide, and sodium ethoxide. Dialkyloxalates suitable for use in the present invention are diethyloxalate and dimethyloxalate. Alcohols suitable for use in the present invention are methanol, ethanol and isopropanol.

The overall process of the invention is illustrated by the following reaction sequence:

dialkyl oxalate + metal alkoxide + alcohol

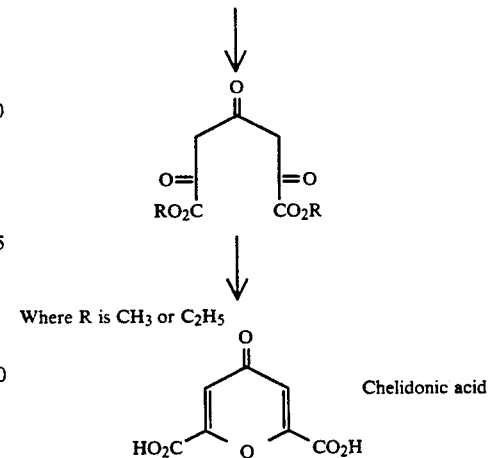

Where R is CH$_3$ or C$_2$H$_5$

Chelidonic acid

EXAMPLE 1

In a 500 ml four neck round bottom flask, fitted with a reflux condenser, mechanical stirrer, liquid dropping funnel and nitrogen atmosphere 37 g(0.253M) of diethyloxolate, 16.46 g(0.232M) of sodium ethoxide and 50 ml of anhydrous ethanol were stirred slowly. 6.4 g(0.11M) of acetone was placed in a dropping funnel and added dropwise to the flask over half an hour. During the hour following the first acetone addition, the reaction temperature was raised slowly to 75° C. Heat was evolved during the reaction and a color change from orange to brown to yellow took place. After 10 to 15 minutes at 75° C. the reaction mixture thickened and was stirred for an additional hour with anhydrous ethanol being added to reduce viscosity. Following this the reaction mixture was cooled to 5° C. by external cooling and mixture of 30 ml of concentrated HCl and 100 g of crushed ice added with vigorous stirring. The resulting mixture was stirred for 30 minutes to ensure that the stirrer broke up any lumps to form a creamy yellow slurry. The solution was then heated to distill off any alcohol and a large portion of the water. 30 ml of concentrated HCl was then added to the flask and the contents refluxed for 24 hours at 100° C. The reaction mixture was then cooled to 5° C. with stirring and then allowed to settle. The product was filtered on a Buchner funnel and washed with a small amount of iced water. The yield of chelidonic acid was 90 to 95%.

The chelidonic acid was converted quantitatively to chelidamic acid by removing product from the filter paper to a reaction vessel and dissolving it in concentrated ammonium hydroxide. The chelidonate/base mixture was refluxed for 6-8 hours and ammonium hydroxide added to keep the pH above 9. The reaction mixture was allowed to cool and then acidified with concentrated HCl and the precipitate filtered cold and washed with small quantities of ice water.

What is claimed is:

1. A process for the manufacture of chelidonic acid comprising the steps of:
   (i) mixing metal alkoxide, dialkyl oxalate and an alcohol together in a reaction vessel;
   (ii) stirring the mixture of (i) while adding acetone at a rate such that the concentration of unreacted acetone in the reaction mixture is not greater than 30% of the dialkyl oxalate and metal alkoxide together;
   (iii) neutralizing the product of (ii) with acid;
   (iv) refluxing to form chelidonic acid.

2. A process as claimed in claim 1 wherein in step (ii) the mixture is heated towards the end of the acetone addition.

3. A process as claimed in claim 1 wherein an excess of alcohol is present during step (ii).

4. A process as claimed in claim 1 with the provision that the neutralized acetone dialkyloxalate is not isolated prior to reflux.

5. A process as claimed in claim 1 wherein the metal alkoxide and dialkyl oxalate are in a molar ratio of 1:1 and alcohol is in excess.

6. A process as claimed in claim 1 wherein the sodium alkoxide, dialkyl oxalate and acetone are in a molar ratio of 2.1:2.1:1.

7. A process as claimed in claim 1 wherein acetone is added at a rate such that the concentration of acetone in the reaction mixture is between 1 and 15% of the total dialkyl oxalate and metal alkoxide together.

8. A process as claimed in claim 1 wherein acetone is added at a rate such that the concentration of acetone in the reaction mixture is between 5 and 10% of the total dialkyl oxalate and metal alkoxide together.

* * * * *